United States Patent [19]

Lee et al.

[11] Patent Number: 5,225,890
[45] Date of Patent: Jul. 6, 1993

[54] SURFACE INSPECTION APPARATUS AND METHOD

[75] Inventors: Ching-Chih Lee, Hudson; James F. Roach, Akron, both of Ohio

[73] Assignee: GenCorp Inc., Fairlawn, Ohio

[21] Appl. No.: 783,949

[22] Filed: Oct. 28, 1991

[51] Int. Cl.[5] ................... G01B 11/30; G01N 21/00
[52] U.S. Cl. .................... 356/371; 356/237; 356/445
[58] Field of Search ........ 356/371, 237, 239, 445–448, 356/30, 31

[56] References Cited

U.S. PATENT DOCUMENTS

| | | |
|---|---|---|
| 2,798,966 | 7/1957 | Summerhayes, Jr. . |
| 3,019,346 | 1/1962 | Laycak . |
| 3,439,988 | 4/1969 | Breske . |
| 3,590,258 | 6/1971 | Shibata et al. . |
| 3,666,370 | 5/1972 | Seasholtz . |
| 3,734,626 | 5/1973 | Roberts et al. . |
| 3,794,427 | 2/1974 | Shibata et al. . |
| 3,797,943 | 3/1974 | Nagao et al. . |
| 3,814,945 | 6/1974 | Allnutt et al. . |
| 3,857,637 | 12/1974 | Obenreder . |
| 3,866,038 | 2/1975 | Korth . |
| 3,871,771 | 3/1975 | Scott . |
| 3,892,494 | 7/1975 | Baker et al. . |
| 3,922,093 | 11/1975 | Dandliker et al. ............... 356/371 |
| 3,976,382 | 8/1976 | Westby . |
| 4,130,361 | 12/1978 | Humphrey . |
| 4,172,666 | 10/1979 | Clarke . |
| 4,207,467 | 6/1980 | Doyle . |
| 4,547,073 | 10/1985 | Kugimiya ........................ 356/371 |
| 4,621,063 | 11/1986 | Wyatt et al. ..................... 356/371 |
| 4,629,319 | 12/1986 | Clarke et al. . |

FOREIGN PATENT DOCUMENTS

| | | |
|---|---|---|
| 2439988 | 3/1976 | Fed. Rep. of Germany . |
| 2095398 | 9/1982 | United Kingdom . |
| 2117897 | 10/1983 | United Kingdom . |
| 2118304 | 10/1983 | United Kingdom . |

*Primary Examiner*—Davis L. Willis
*Assistant Examiner*—Hoa Q. Pham

[57] ABSTRACT

An apparatus for inspecting a reflective surface of an article for defects includes a point light source for generally uniformly illuminating the entire surface of the article under inspection, and a diffusing screen for intercepting the light rays reflected from the surface under inspection of the article. The intercepted light rays produce a high resolution image on the screen consisting of bright and dark areas or spots corresponding to surface defects in the article under inspection.

10 Claims, 3 Drawing Sheets

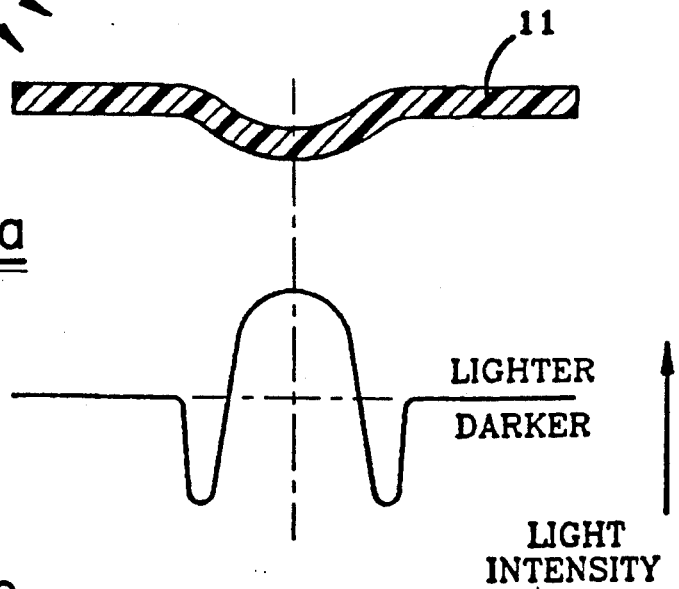
FIG.-2a
FIG.-2b
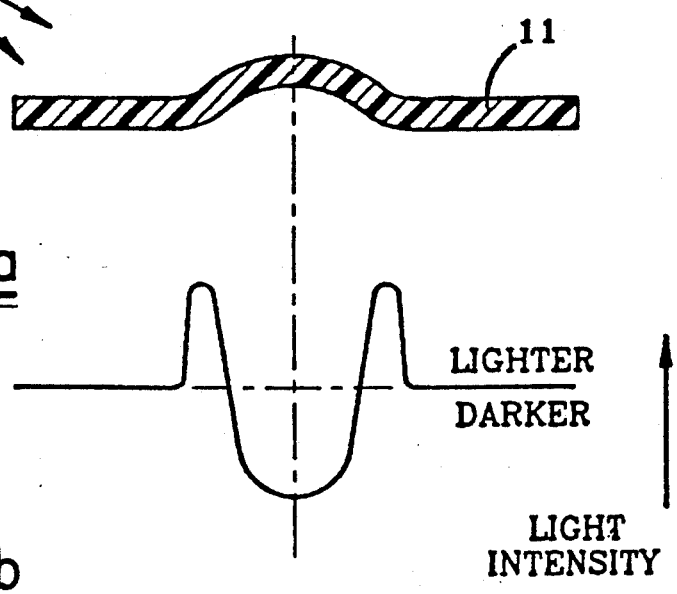
FIG.-3a
FIG.-3b

SURFACE INSPECTION APPARATUS AND METHOD

FIELD OF THE INVENTION

The invention relates to an apparatus and method for surface inspection, and in particular to an apparatus and method which is simple, fast, easy to use, and which gives a definite, easy-to-interpret result. More particularly, the invention relates to such an apparatus and method for inspecting any surface where smoothness or lack of defects is of concern.

BACKGROUND

The surface smoothness of exterior body panels is an important consideration in the automotive industry. In order to study changes in the surface quality of these exterior body panels resulting from new material formulation and processing techniques, and for quality control in the plant production area, it is necessary to have a fast and accurate inspection which provides easy-to-interpret results.

Prior art methods accomplish surface inspection by examining one or more line profiles or images reflected off the surface under inspection. Generally, they fail to thoroughly inspect the entire surface during a single examination. Such line profiling or imaging apparatus and methods which provide discrete rather than continuous or full-field surface information include the back-lighted grid method, green-room inspection and laser beam traces. Mechanical profiling of the type carried out with a stylus similarly provide discrete rather than full-field results.

The closest known prior art is disclosed in Breske, U.S. Pat. No. 3,439,988, which discloses an apparatus for inspecting a reflective surface, comprising a slide projector for projecting one or more light or dark lines onto the reflective surface under inspection, and a screen positioned for intercepting the reflected light rays and displaying the line image. The Breske apparatus for surface inspection uses a slide having one or more discrete lines to uncover surface defects. Breske also contemplates illuminating an entire surface to permit an overall inspection of any reflective surface (see column 3, lines 37-42 and column 4, line 1). However, it is important to note that this teaching is made in the context of utilizing a slide projector, wherein the slide projector includes a light source and a lens for focusing an image. The positioning of the light source and lens in a slide projector arrangement effectively makes the Breske light source an extended light source.

In contrast, the present invention uses a point light source, whereby the results achieved by the apparatus and method of the present invention are superior to those which can be realized by the Breske apparatus and method when an entire surface under inspection is illuminated. Moreover, in order for Breske to obtain a sharp image, a fixed distance between the lens and screen must be adhered to for a given lens setting, while in comparison, the screen of the present invention can be positioned within a range of distances from the object under inspection, without adversely affecting the results obtained.

SUMMARY OF THE INVENTION

Objectives of the present invention include providing an apparatus and method for surface inspection which is simple, fast, inexpensive and easy to use, which provides an accurate and easy-to-interpret result and which examines the entire surface of an article under inspection.

These objectives are achieved by the apparatus of the present invention for inspecting a reflective surface of an article for defects, comprising, a point light source for illuminating the surface of the article under inspection, and a diffusing screen for intercepting reflected light rays from the illuminated article, the diffusing screen and the light source being disposed on generally opposite sides of the surface under inspection, so that an image of a light intensity profile of the article is produced on the screen.

The method comprises illuminating the surface under inspection of the article with the point light source, and intercepting reflected light rays from the illuminated surface with the diffusing screen, so that an image of a light intensity profile of the reflective surface of the article is produced on the screen.

BRIEF DESCRIPTION OF THE DRAWINGS

FIGS. 2(a) and 2(b) is a diagrammatic representation of the image of the light intensity profile produced by a single depression-type defect in a generally flat surface under inspection;

FIGS. 3(a) and 3(b) is a diagrammatic representation of the image of the light intensity profile produced by a single bump-type defect in a surface under inspection;

Similar numerals refer to similar parts throughout the drawings.

DETAILED DESCRIPTION OF THE INVENTION

Figure 1:
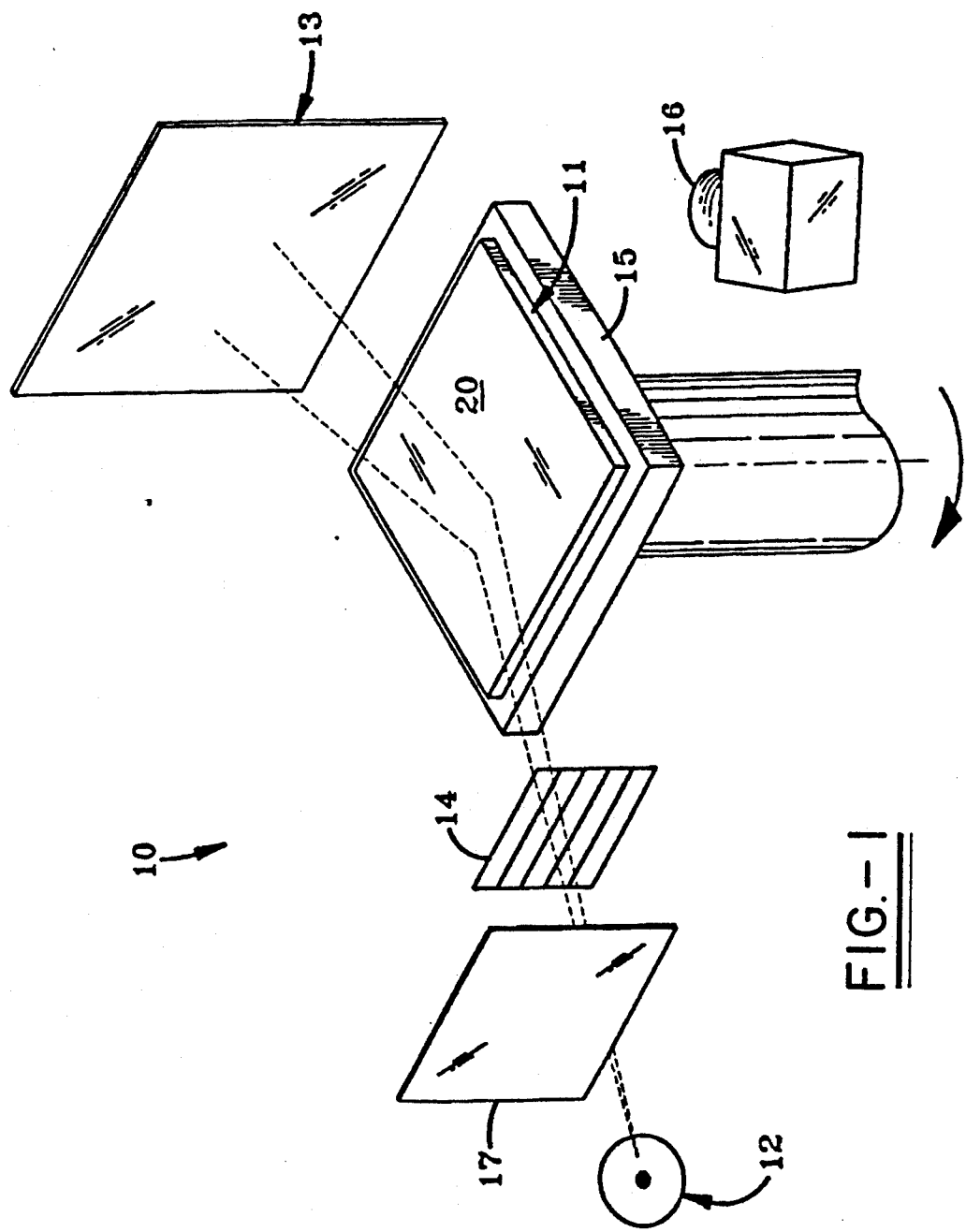
FIG. 1 is a diagrammatic view of the surface inspection apparatus shown in its intended use.

The apparatus of the present invention is indicated generally at 10 and is shown in FIG. 1 in its intended use of inspecting a reflective surface 20 of a part 11. Apparatus 10 includes a point light source 12 and a diffusing screen 13. Point light source 12 is one producing divergent light rays for illuminating an entire surface to be inspected. Examples of suitable point light sources include a small high intensity lamp, a microfilm projector lamp, a spark or arc light source, or any other type of lamp wherein the light emitted from the lamp originates from a very small region, and diverges to uniformly illuminate a reflective surface of a part under inspection. A preferred point light source is a microfilm projector lamp manufactured by GTE Corporation, 1 Stamford Forum, Stamford, Conn. 06904, and identified as Sylvania lamp model XD10 EHJ. Alternatively, point light source 12 could be simulated using a laser/lens combination wherein the lens expands the rays of the laser and effectively acts as a beam expander. Examples of other suitable simulated point light sources as defined include an extended light source/lens combination wherein the lens focuses the extended light source such as a bulb having a long filament. A preferred simulated point light source for use in the present invention is the laser/lens combination. The point light source chosen depends on the particular application in which apparatus 10 of the present invention is used.

Screen 13 is a diffusing screen. A diffusing screen is one in which light rays are emitted in all directions after an incident light beam impinges on the screen. The diffusing screen has a smooth surface, such as unpainted drywall, Bristol board, or the like. Screen 13 may be flat or curved depending on the particular application which is used. Choice is also application dependent.

An optional blocking screen 17 for preventing any stray non-reflected light rays from travelling directly from light source 12 to diffusing screen 13 is disposed in a suitable position between the light source and screen 13 (FIG. 1). Impingement of such stray light on screen 13 typically adversely affects the quality of the image produced thereon. While the use of blocking screen 17 is optional, it is preferred for most point light sources other than simulated point light sources.

As further shown in FIG. 1, an optional grill 14 can be disposed between point light source 12 and reflective part 11 to provide discrete line profiles of the surface of part 11 under inspection. Part 11 is placed on a turntable 15 for sequentially producing on screen 13 a plurality of images of certain defects, which are particularly sensitive to the orientation of the defect with respect to the direction of travel of incident light from light source 12. An optional camera or video recorder 16 can be positioned for registering the images produced on screen 13. The functions of optional grill, turntable, camera or video recorder 16, and blocking screen 14-17, will be further explained below in the description of the operation of inspection apparatus 10.

The distance of point light source 12 from part 11 and the distance of diffusing screen 13 from part 11 are independent of each other and are each totally application dependent.

To operate apparatus 10 selected point light source 12 is illuminated and the light rays from the source diverge and uniformly illuminate the entire reflective surface 20 under inspection. The diverging light rays in turn are reflected from part 11 and intercepted by diffusing screen 13. If reflective surface 20 of part 11 is perfectly flat, the image produced on screen 13 should exhibit nearly uniform light intensity. If, on the other hand, reflective surface 20 of part 11 has a designed contour but is very smooth, the light intensity in the produced image should have a corresponding smooth variation. However, if defects exist in reflective surface 20 of part 11, the image produced on screen 13 would exhibit a corresponding anomaly in the light intensity. A concave area generally would cause the reflected light rays to converge, while a convex area would generally cause the reflected light rays to diverge. Thus, a depression on an otherwise generally flat surface consisting of a flat-convex-concave-convex-flat profile, would yield a corresponding regular-dark-bright-dark-regular light intensity profile, as shown diagrammatically in FIG. 2. In contrast, a bump having a flat-concave-convex-concave-flat profile would yield a regular-bright-dark-bright-regular light intensity variation, as shown diagrammatically in FIG. 3. Defects such as scratches, a scrubbed area comprising a large number of compact scratches, dirt pimples, etc., can be revealed due to the change in reflectivity or surface profile causing light intensity variations of the type described immediately above. Other common surface defects such as long and short-term waviness, orange peel, blister, porosity, sink marks, read-outs, and the like, can also be observed using surface inspection apparatus 10.

The images produced on screen 13, such as those due to long-term surface waviness and bond-line-read-out, are especially dependent on the orientation of part 11 with respect to the incident light rays emitted from source 12, due to the directional nature of such defects. To increase efficiency when inspecting parts, turntable 15 is employed to support and continuously or selectively rotate part 11.

The image produced on screen 3 can be viewed by the naked eye of an observer, or by optional camera or video recorder 16 for instantaneous or subsequent analysis. Alternatively, optional camera or video recorder 16 may be connected to a computer for data acquisition, storage and/or print-out useful in immediate or subsequent analysis. Computers are particularly useful in production line applications. However, it is important to note that for a video recorder, if utilized, to register the image, the light intensity of the image produced must be sufficiently high.

Optional grill 14 can be disposed between point light source 12 and part 11 so t hat every line on the grill blocks a line of light from the point light source from impinging on reflective surface 20 under inspection of part 11. The unobstructed diverging light rays which do pass through grill 14 are reflected off surface 20 of part 11 and are intercepted by diffusing screen 13, and the dark lines caused by grill 14 and produced on the screen will indicate the surface waviness at the dark line locations on the part surface, which is similar to the result obtainable by a laser beam scanning method. Grill 14 preferably is placed close to part 11 to minimize the effect of diffused light. The inclination of grill 14 can be adjusted to vary the dark line thickness and spacings.

The invention will be better understood by the following example.

EXAMPLE 1 (PRESENT INVENTION)

Figure 4:
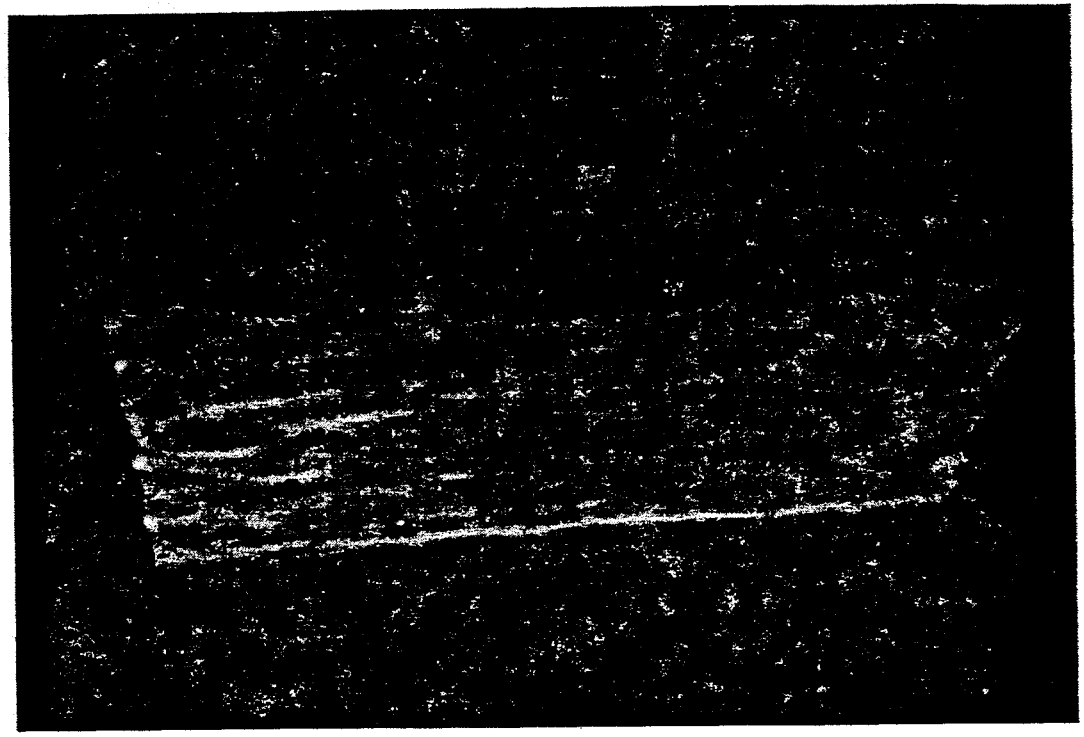
FIG. 4 is a photograph of the image of the light intensity profile produced from a flat painted fiber-reinforced plastic panel using the apparatus and method of the present invention.

A microfilm projector lamp contained in an enclosure was utilized as the point light source, and a piece of cardboard was utilized as the blocking screen. A large piece of poster board taped onto a vertical wall served as the diffusing screen. A blower was utilized to prevent overheating of the lamp. The lamp was illuminated and positioned so that a flat painted fiber-reinforced plastic panel had its reflective surface under inspection uniformly illuminated. The diverging light rays from the lamp in turn were reflected from the part. The reflected light rays were then intercepted by the diffusing screen and an image exhibiting a light intensity profile was produced on the screen as shown in the photograph denoted FIG. 4. It should be noted that the resolution of the image shown in FIG. 4 is very high.

EXAMPLE 2 (COMPARATIVE)

Figure 5:
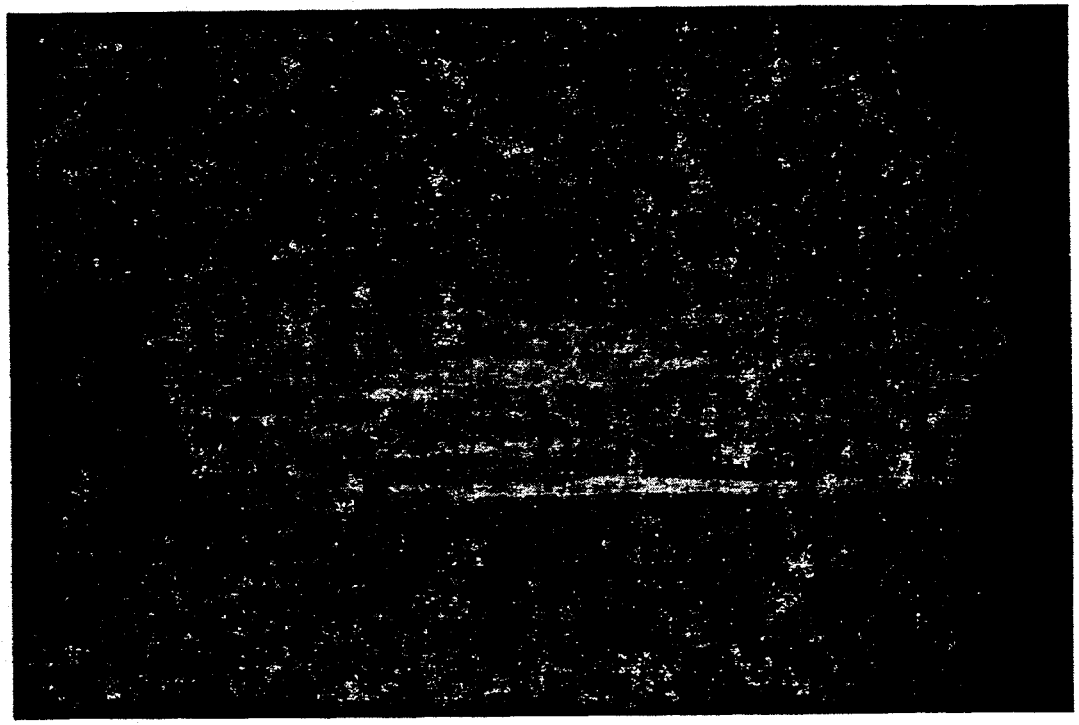
FIG. 5 is a photograph of the image of the light intensity profile produced from the panel of FIG. 4 using the apparatus and method disclosed in Breske, U.S. Pat. No. 3,439,988.

The apparatus and method taught in Breske, U.S. Pat. No. 3,439,988 were utilized. A clear slide as described in column 3, line 33 through column 4, line 1, was placed in the slide projector for illuminating the entire surface of the same panel used in Example 1. The image produced on the screen is shown in the photograph denoted FIG. 5. It can clearly be seen that the resolution of the image produced by following the teachings of Breske, is clearly inferior to that produced in Example 1 by the apparatus and method of the present invention.

The surface inspection apparatus and method of the present invention is useful for inspecting any surface where smoothness or lack of defects is of concern. The present invention allows examination of the entire reflective surface of an article under inspection, and is simple, fast, inexpensive and easy to use, and provides an accurate and easy-to-interpret result. The surface inspection apparatus and method has utility in uncovering a variety of defects in a surface being inspected, including long and short-term waviness, scratches, scrubbed area, orange peel, blister, porosity, sink marks, read-outs, and the like, which are well known to those having ordinary skill in the art.

While in accordance with the Patent Statutes, the best mode and preferred embodiment has been set forth, the scope of the invention is not limited thereto, but rather by the scope of the attached claims.

What is claimed is:

1. An apparatus for inspecting a reflective surface of an article for defects, said apparatus comprising:
   a) a point light source for illuminating said surface;
   b) a diffusing screen for intercepting reflected light rays from said surface, said diffusing screen and said light source being disposed on generally opposite sides of said surface, so that an image of a light intensity profile of said surface is produced on said screen; and
   c) turntable means for rotating the article, the surface of which is to be inspected, to change the direction from which incident light rays from the point light source impinge on the surface defects, said apparatus being free of optical means for focusing light rays emitted from the point light source.

2. The apparatus of claim 1, wherein light source emits divergent light rays for generally uniformly illuminating the entire surface under inspection; and wherein the diffusing screen is a screen which emits intercepted light rays from said surface in all directions.

3. The apparatus of claim 2, wherein optional blocking means are disposed generally between the point light source and the diffusing screen for preventing stray non-reflected light rays from travelling directly from said light source to said screen.

4. The apparatus of claim 2, wherein optional camera or video recorder means is positioned for registering the image produced on the diffusing screen.

5. The apparatus of claim 2, wherein optional grill means are disposed generally between the point light source and the surface of the article under inspection for producing line profile images on the screen for providing discrete information on defects in said surface under inspection.

6. A method of inspecting a reflective surface of an article for defects, said method comprising the steps of:
   a) positioning a point light source and a diffusing screen on generally opposite sides of the reflective surface under inspection;
   b) illuminating the surface under inspection with said point light source;
   c) intercepting reflected light rays from said illuminated surface with said diffusing screen, so that an image of a light intensity profile of said reflective surface is produced on said screen; and
   d) changing the orientation of the article to change the direction from which incident light rays from the point light source impinge on the surface defects, said method being free of utilizing means to focus the light rays emitted from the point light source.

7. The method of claim 6, including the step of generally uniformly illuminating the entire surface under inspection of the article.

8. The method of claim 7, including the step of blocking stray non-reflected light rays from travelling directly from the point light source to the diffusing screen.

9. The method of claim 7, including the step of registering the image produced on the diffusing screen.

10. The method of claim 7, including the step of producing line profile images on the screen for providing discrete information on defects in the surface under inspection.

* * * * *